United States Patent
O'Connor et al.

(10) Patent No.: US 10,617,820 B2
(45) Date of Patent: Apr. 14, 2020

(54) FLUID RESTRICTION MECHANISMS FOR DRUG DELIVERY PUMPS

(71) Applicant: UNL Holdings LLC, New York, NY (US)

(72) Inventors: Sean M. O'Connor, West Chester, PA (US); Ian B. Hanson, Wayne, PA (US); Paul F. Bente, IV, Wayne, PA (US); Matthew J. Clemente, Downingtown, PA (US)

(73) Assignee: UNL Holdings LLC, New York, NY (US)

( * ) Notice: Subject to any disclaimer, the term of this patent is extended or adjusted under 35 U.S.C. 154(b) by 690 days.

(21) Appl. No.: 14/761,853

(22) PCT Filed: Jan. 24, 2014

(86) PCT No.: PCT/US2014/013019
§ 371 (c)(1),
(2) Date: Jul. 17, 2015

(87) PCT Pub. No.: WO2014/116998
PCT Pub. Date: Jul. 31, 2014

(65) Prior Publication Data
US 2015/0359965 A1 Dec. 17, 2015

Related U.S. Application Data

(60) Provisional application No. 61/756,556, filed on Jan. 25, 2013.

(51) Int. Cl.
*A61M 5/168* (2006.01)
*A61M 5/145* (2006.01)
(Continued)

(52) U.S. Cl.
CPC ........ *A61M 5/16813* (2013.01); *A61M 5/141* (2013.01); *A61M 5/1452* (2013.01);
(Continued)

(58) Field of Classification Search
CPC .............. A61M 5/16813; A61M 5/141; A61M 5/14248; A61M 5/16822; A61M 5/1454; A61M 5/16877; A61M 2205/3334
See application file for complete search history.

(56) References Cited

U.S. PATENT DOCUMENTS 3,631,654 A * 1/1972 Riely .................... A61M 5/165
210/446
5,147,311 A 9/1992 Pickhard
(Continued)

FOREIGN PATENT DOCUMENTS

EP 1559442 A2 8/2005

OTHER PUBLICATIONS

European Patent Office, International Search Report and Written Opinion from International PCT Application No. PCT/US2014/013019 dated Aug. 14, 2014, 17 pgs.

*Primary Examiner* — Nathan R Price
*Assistant Examiner* — Justin L Zamory
(74) *Attorney, Agent, or Firm* — Hamilton, Brook, Smith & Reynolds, P.C.

(57) ABSTRACT

A replaceable fluid restriction mechanism includes: an aperture residing adjacent to a fluid pathway connection and configured to permit flow of a drug fluid through the aperture when the fluid pathway connection is open; an entry point of a fluid channel configured such that the flow of drug fluid can travel through aperture to the entry point and through the fluid channel to an exit point; and an outlet aperture of a port through which the flow of drug fluid may travel after exiting the exit point, wherein a fluid conduit is connected to the
(Continued)

fluid restriction mechanism at the outlet aperture. A configurable fluid restriction mechanism includes a plurality of fluid channels, selectable to align with the entry point and an exit point of the fluid restriction mechanism.

14 Claims, 7 Drawing Sheets

(51) Int. Cl.
*A61M 5/14* (2006.01)
*A61M 5/142* (2006.01)

(52) U.S. Cl.
CPC .... *A61M 5/14248* (2013.01); *A61M 5/16822* (2013.01); *A61M 5/1454* (2013.01); *A61M 2205/13* (2013.01)

(56) References Cited

U.S. PATENT DOCUMENTS

| | | |
|---|---|---|
| 2005/0038387 A1 | 2/2005 | Kriesel et al. |
| 2005/0171491 A1* | 8/2005 | Minh Miner ........ A61M 5/1411 604/257 |
| 2005/0277882 A1* | 12/2005 | Kriesel ............. A61M 5/14244 604/131 |
| 2005/0277883 A1 | 12/2005 | Kriesel |
| 2006/0195057 A1 | 8/2006 | Kriesel et al. |
| 2007/0219502 A1* | 9/2007 | Kriesel ................ A61M 5/148 604/185 |
| 2008/0027386 A1 | 1/2008 | Kriesel et al. |
| 2009/0093792 A1* | 4/2009 | Gross ................ A61M 5/14566 604/518 |
| 2010/0312187 A1 | 12/2010 | Kriesel et al. |

* cited by examiner

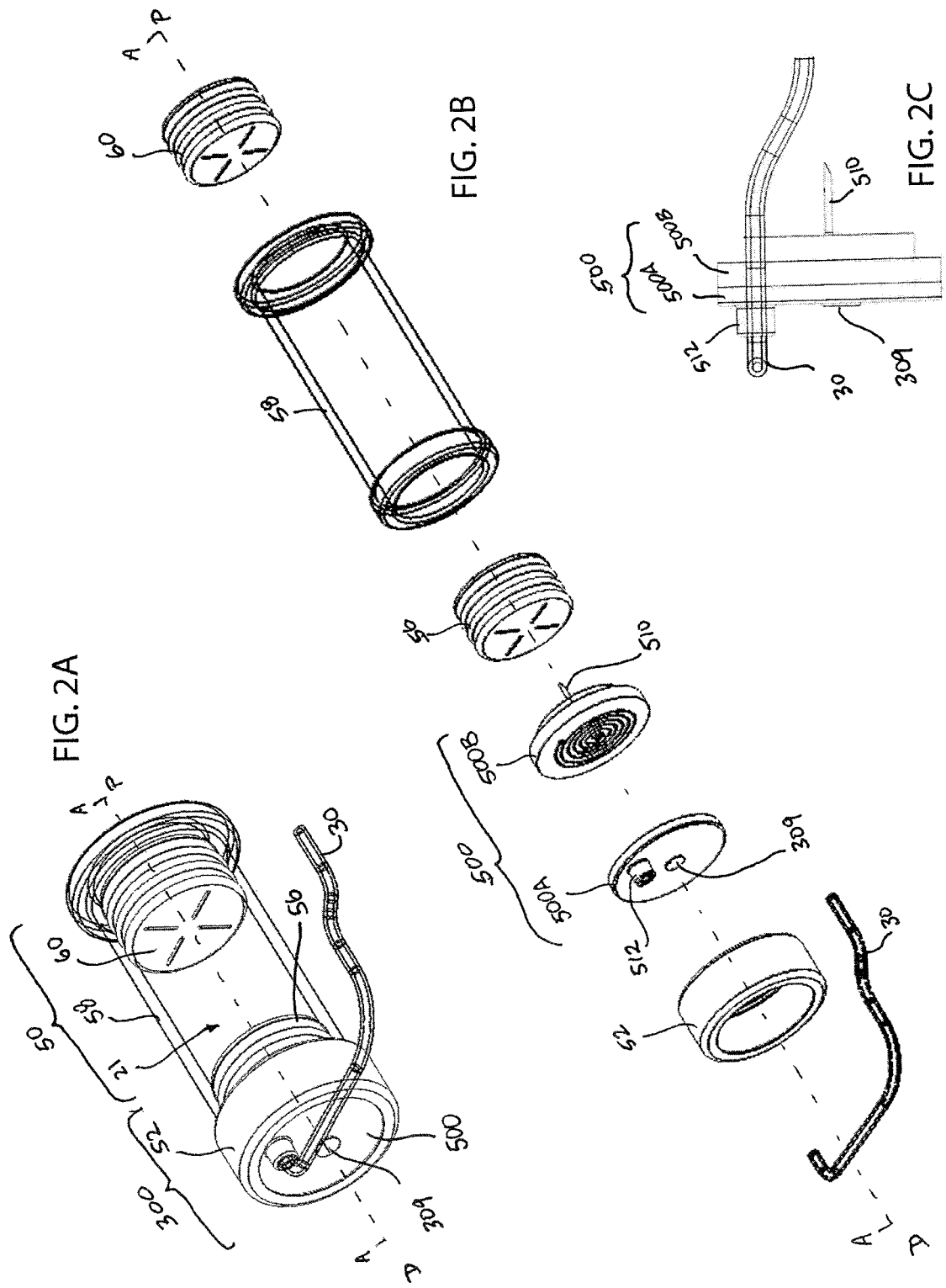

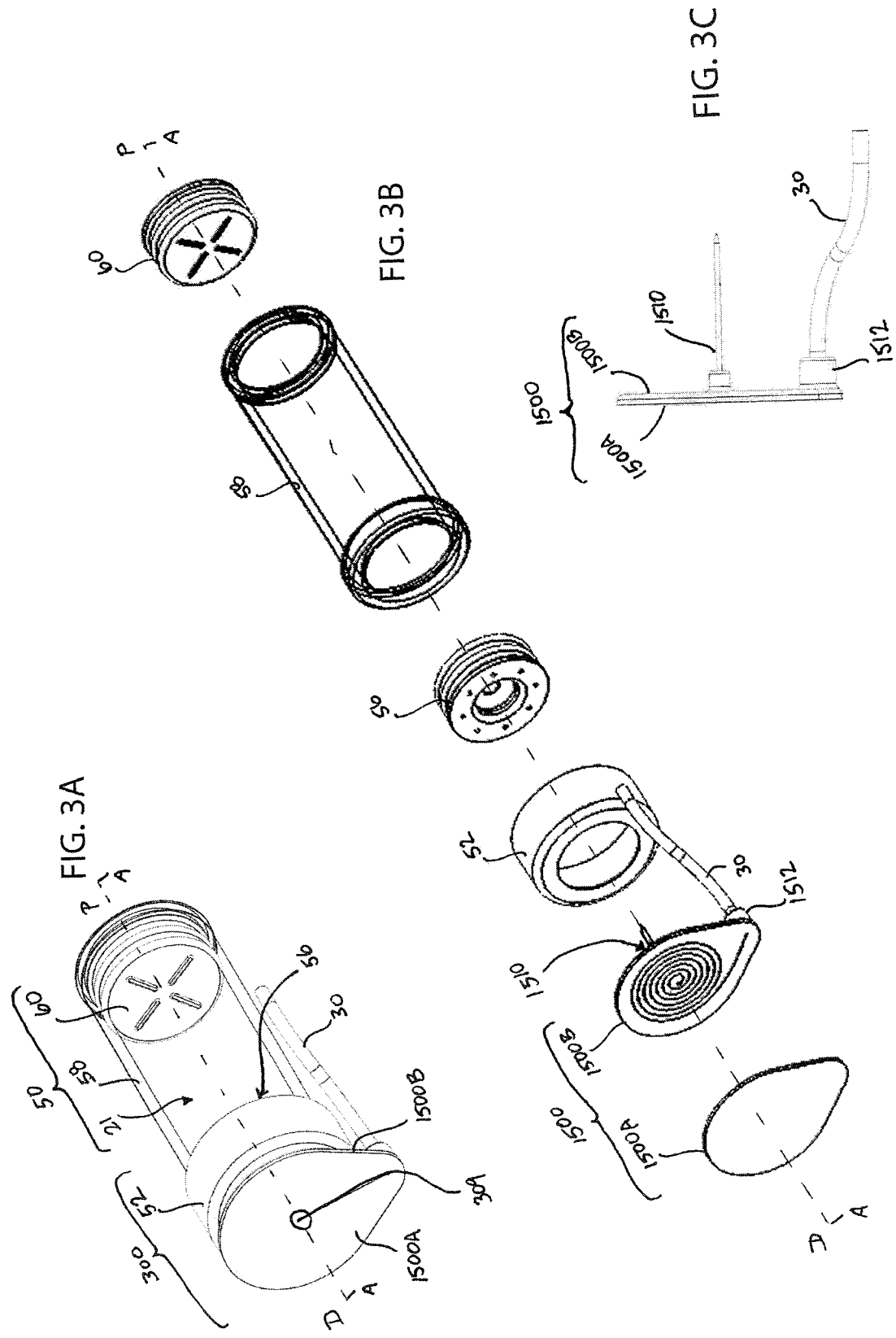

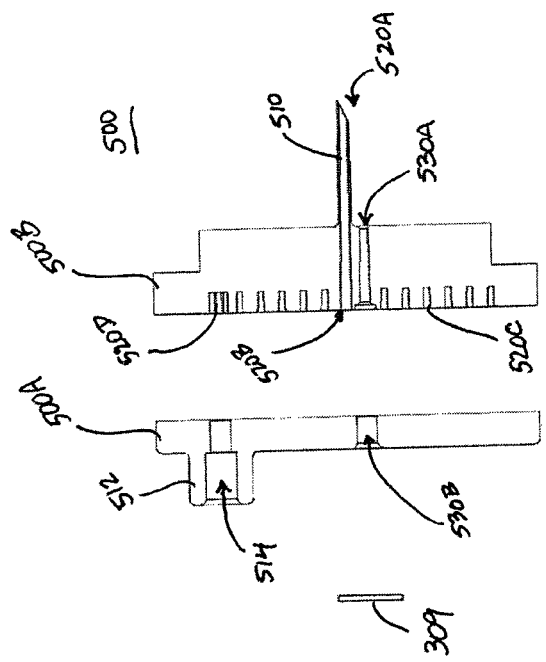
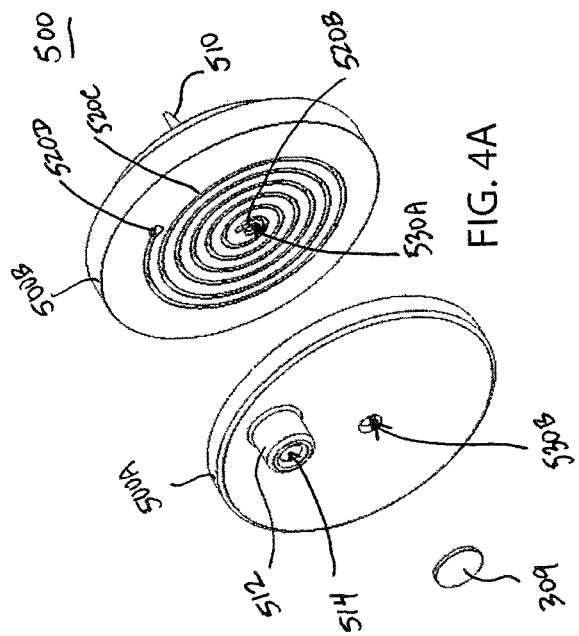
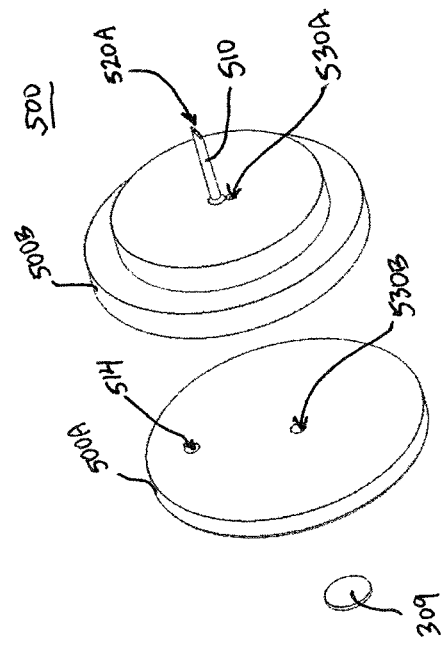
FIG. 4C
FIG. 4A
FIG. 4B

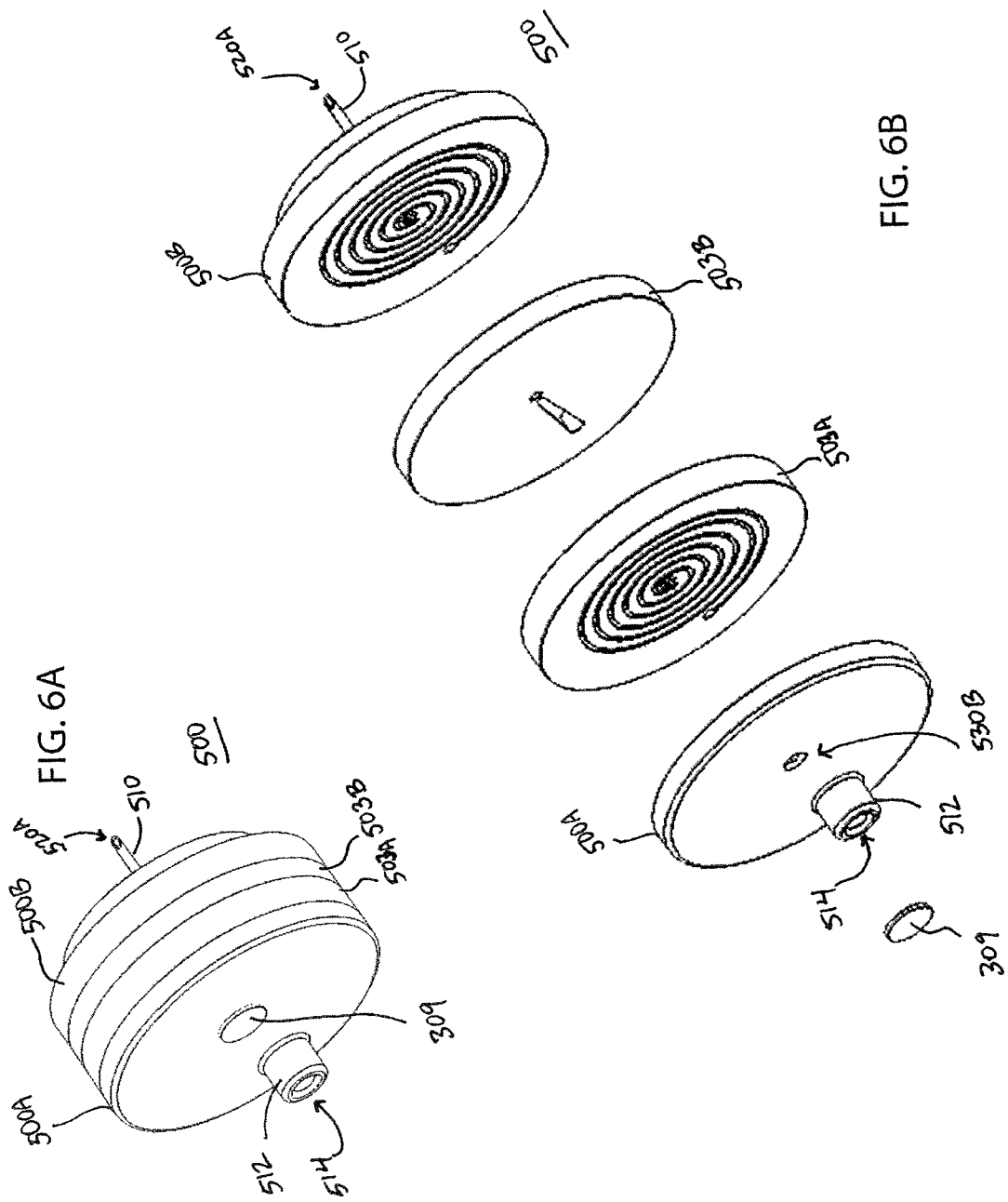

FLUID RESTRICTION MECHANISMS FOR DRUG DELIVERY PUMPS

CROSS-REFERENCE TO RELATED APPLICATIONS

This application is a national phase application of application PCT/US2014/013019 filed Jan. 24, 2014 under the Patent Cooperation Treaty, and which claims priority to U.S. Provisional Application No. 61/756,556, filed on Jan. 25, 2013, both of which are included by reference herein in their entireties for all purposes.

FIELD

THIS INVENTION relates to drug delivery pumps. More particularly, this invention relates to fluid restriction mechanisms for the controlled delivery of drug substances and drug delivery pumps which incorporate such fluid restriction mechanisms.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for a configurable drug delivery system that is precise and reliable and can offer clinicians and patients a small, low cost, light weight, simple to use alternative for parenteral delivery of liquid medicines.

SUMMARY

The embodiments of the present invention provide selectably replaceable, configurable, and/or stackable fluid restriction mechanisms for use within a drug delivery pump system. The fluid restriction mechanisms may include one or more selectable fluid pathways or channels to meet a range of desired fluid restriction parameters. Each restriction mechanism may have multiple selectable pathways, or a single pathway with passages that may be opened or closed to modify the fluid pathway prior to assembly. The fluid restriction plates may also include permeable membranes to permit venting of gaseous fluids from the fluid pathway. The pump type drug delivery systems which include such fluid pathway systems and fluid restriction mechanisms are capable of being primed to reduce or eliminate gaseous fluids from the fluid pathway system prior to introduction of a liquid fluid to a patient. When delivering fluid subcutaneously it is important to minimize or eliminate the amount of gaseous fluid that is delivered into the patient. Delivery of gaseous fluids, such as air or inert gases, is correlated to increased perception of pain for patients and may adversely affect absorption profiles of pharmaceutical treatments. As such, it is important to minimize or eliminate such gaseous fluids from the system prior to injection of the drug. The fluid restriction mechanisms are also easily configurable to permit the manufacture of one type of mechanism (e.g., plate, chip, etc.) while enabling customization of the fluid restriction mechanism prior to or during assembly to enable a range of fluid restriction parameters.

As described herein, a single restriction mechanism may have a number of selectable fluid pathways or channels with different restriction parameters. Based on the desired fluid flow characteristics, the manufacturer or assembler can select the appropriate fluid pathway and assemble the components such that the desired fluid pathway is utilized. Similarly, the fluid pathways may be opened or closed by the assembler/manufacturer to enable longer or shorter fluid pathways, as may be desired to meet the particular flow characteristics. While these are important and desirable features of drug delivery devices, such features should not be cumbersome or complicated for the user. The inventors of the present invention have developed a system which enables the configurability of the fluid restriction mechanisms and also the reduction or elimination of gaseous fluids from the fluid pathway, but yet is easy to use for clinicians and patients.

When delivering fluid subcutaneously it is important to control or restrict the flow of fluid that is delivered into the patient. A drug pump, such as an infusion pump or a bolus injector, may be needed to deliver a particular amount of drug fluid within a period of time. The flow of drug fluid, however, may need to be restricted as it passes through the system from a drug container to the needle insertion mechanism and into the patient. Some drug pump systems may utilize one or more an active fluid restriction mechanisms, one or more passive fluid restriction mechanisms, or a combination of both. The present invention provides configurable fluid restriction mechanisms (e.g., plates, chips, etc.) for microfluidic pathways which can be readily integrated into a pump type delivery device within the fluid pathway between the drug container and the needle insertion mechanism.

The pump type delivery devices may be connected in fluid flow communication to a patient or user, for example, through any suitable hollow tubing. The hollow tubing may be connected to a hollow needle that is designed to pierce the skin of the patient and to deliver a fluidic medium therethrough. Alternatively, the hollow tubing may be connected directly to the patient as through a cannula, or the like. As a further option, a solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, microneedle array, or infusion set tubing. The flow of fluid may be initiated by a number of different drive mechanisms which push a plunger seal within a drug container, thereby forcing a drug fluid out of the drug container. In at least one embodiment, the drive mechanism may be a spring-based drive mechanism that utilizes one or more springs to drive or push the plunger seal. The activation of the drive mechanism and the pushing of the plunger seal may occur before or after a fluid connection is completed, or itself may first cause a fluid connection to be made before forcing fluid through the fluid connection. Once the fluid flow is initiated, the fluid restriction mechanisms of the present invention may be utilized to control the duration of fluid flow through the drug pump. The fluid restriction mechanism may be located between the drug container and the fluid conduit leading to the insertion mechanism, or at one or more locations within the fluid pathway from drug container to patient through the insertion mechanism.

In a first embodiment, the present invention provides a selectively replaceable fluid restriction mechanism for a drug delivery pump. The fluid restriction mechanism includes an aperture residing adjacent to a fluid pathway connection and configured to permit flow of a drug fluid through the aperture when the fluid pathway connection is open; an entry point of a fluid channel configured such that the flow of drug fluid can travel through aperture to the entry point and through the fluid channel to an exit point; and an outlet aperture of a port through which the flow of drug fluid may travel after exiting the exit point, wherein a fluid conduit is connected to the fluid restriction mechanism at the outlet aperture. The selectively replaceable fluid restriction mechanism may further include a vent aperture to vent air or gas from a proximal side of the fluid restriction mechanism to a distal side of the fluid restriction mechanism; and a membrane to facilitate the passage of air or gas in one direction while preventing fluid passage therethrough. The membrane may be a permeable membrane.

In another embodiment, the present invention provides a configurable fluid restriction mechanism for a drug delivery pump which includes an aperture residing adjacent to a fluid pathway connection and configured to permit flow of a drug fluid through the aperture when the fluid pathway connection is open; an entry point configured such that the flow of drug fluid can travel through aperture to the entry point; a plurality of fluid channels, selectable to align with the entry point and an exit point of the fluid restriction mechanism; and an outlet aperture of a port through which the flow of drug fluid may travel after exiting the exit point, wherein a fluid conduit is connected to the fluid restriction mechanism at the outlet aperture. The configurable fluid restriction mechanism may include a vent aperture to vent air or gas from a proximal side of the fluid restriction mechanism to a distal side of the fluid restriction mechanism; and a membrane to facilitate the passage of air or gas in one direction while preventing fluid passage therethrough. The plurality of fluid channels may vary in length to provide different durations of travel for the flow of drug fluid, and/or the plurality of fluid channels may vary in diameter to provide different fluid restrictions to the flow of drug fluid.

In at least one embodiment, a plurality of the configurable fluid restriction mechanisms may be connected in series in a stacked configuration, and wherein the aperture of the first fluid restriction mechanism resides adjacent to a fluid pathway connection and configured to permit flow of a drug fluid through the aperture when the fluid pathway connection is open, and the fluid conduit is connected to the outlet aperture of the last fluid restriction mechanism in the stacked configuration. In another embodiment, the one or more fluid channels may be selectively opened to permit the flow of drug fluid, and/or selectively closed to prevent the flow of drug fluid. In at least one embodiment, one or more fluid channels may be connected to each other to increase the duration of travel that the drug fluid must flow through. The fluid restriction mechanisms may be in the shape of a disc, a spheroid, a square, a sphere, a cube, a rectangle, or a pyramid.

In yet another embodiment, the present invention provides a drug delivery pump with fluid delivery control which includes a housing, within which an activation mechanism, an insertion mechanism, a drug container having a plunger seal may be mounted, and one or more of the fluid restriction mechanisms described above, wherein the drug container is connected at one end to a drive mechanism and at another end to a fluid pathway connection, and the fluid restriction mechanism is connected at one end to the fluid pathway connection and at the other end to a fluid conduit, and the fluid conduit is connected at another end to the insertion mechanism; such that the fluid restriction mechanism is configured to restrict or control a flow of a drug fluid from the drug container to the insertion mechanism. The fluid restriction mechanism may be a component of the fluid pathway connection mounted to and integrated within the barrel of a drug container, or the fluid restriction mechanism may be a component adjacent to the fluid pathway connection and configured to restrict the flow of drug fluid from the barrel of a drug container through the drug pump once the fluid pathway connection is opened. Alternatively, the fluid restriction mechanism may be connected to the fluid pathway connection by a first fluid conduit, and the fluid restriction mechanism is connected to the insertion mechanism by a second fluid conduit, such that the flow of drug fluid is restricted between the drug container and the insertion mechanism by the fluid restriction mechanism.

The novel embodiments of the present invention provide fluid restriction mechanisms which are capable of controlling, providing resistance, or otherwise preventing free fluid flow of a drug substance out of a drug container and, thereby, controlling the rate of delivery of drug substances. The present invention also provides drug pumps which utilize such fluid restriction mechanisms. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include or utilizes one or more additional components which may be considered standard components in the industry of medical devices. For example, the embodiments may utilize certain medical grade adhesives to affix components together. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 2A shows an isometric view of a fluid restriction mechanism, according to at least one embodiment of the present invention, attached to an integrated sterile fluid pathway connection and drug container;

FIG. 2B shows an exploded isometric view of the fluid restriction mechanism, and integrated sterile fluid pathway connection and drug container, shown in FIG. 2A;

FIG. 2C shows a side view of the fluid restriction mechanism shown in FIG. 2A;

FIG. 3A shows an isometric view of a fluid restriction mechanism, according to another embodiment of the present invention, attached to a sterile fluid pathway connection which may or may not be integrated within the drug container;

FIG. 3B shows an exploded isometric view of the fluid restriction mechanism, and sterile fluid pathway connection and drug container, shown in FIG. 3A;

FIG. 3C shows a side view of the fluid restriction mechanism shown in FIG. 3A;

FIG. 4A shows an exploded isometric view of the fluid restriction mechanism shown in FIGS. 2A-2C;

FIG. 4B shows another angle of the exploded isometric view of the fluid restriction mechanism shown in FIG. 4A;

FIG. 4C shows a cross-sectional view of the fluid restriction mechanism shown in FIGS. 4A-4B;

FIG. 6A shows an isometric view of a stackable fluid restriction mechanism, according to another embodiment of the present invention;

FIG. 6B shows an exploded isometric view of the stackable fluid restriction mechanism shown in FIG. 6A;

DETAILED DESCRIPTION

Figure 1A:
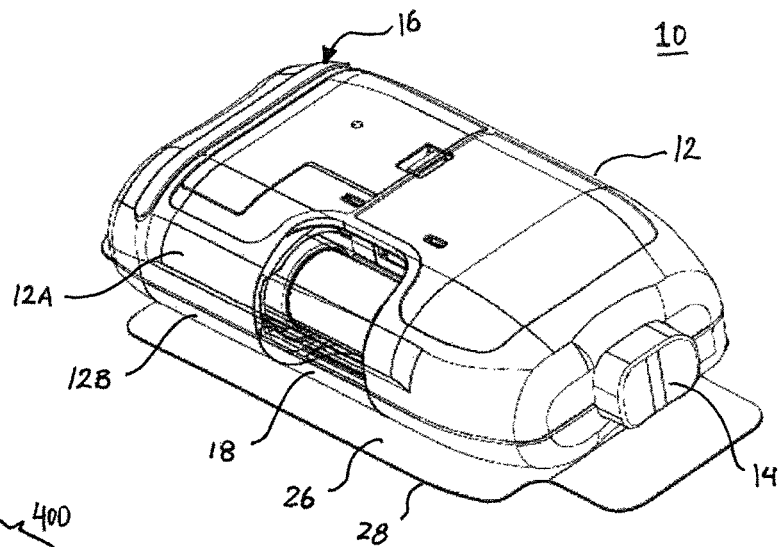
FIG. 1A shows an isometric view of a drug delivery pump having a fluid restriction mechanism, according to one embodiment of the present invention.

The present invention provides fluid restriction mechanisms for the controlled delivery of drug substances and drug delivery pumps which incorporate such fluid restriction mechanisms. The fluid restriction mechanisms of the present invention control the rate of drug delivery by providing resistance and/or increasing the length of the fluid delivery pathway from the drug container to the needle insertion mechanism, for drug delivery into the patient. Additionally, the fluid restriction mechanisms of the present invention may be readily replaceable, configurable, and/or stackable to provide a range of fluid pathways and to meet a myriad of drug delivery needs. For example, the manufacturer, drug-filler, assembler, or another member of the production process may select and insert the necessary fluid restriction mechanism to meet the desired drug delivery profile. This selection and insertion may be performed by initial placement or replacement of the fluid restriction mechanism. Additionally or alternatively, this may be performed by adjusting the fluid restriction mechanism, such as by rotation of a configurable fluid restriction mechanism having a plurality of fluid pathway channels or by open the desired fluid pathway channels of a multi-channel mechanism. Additionally or alternatively, the fluid delivery profile may be met by utilizing a multitude of fluid restriction mechanisms, at least in part, in a series configuration or in a parallel configuration. Each of these variations of the fluid restriction mechanism may be utilized to meet the desired fluid delivery profile from the drug delivery pump.

As used herein to describe the fluid restriction mechanisms, drug delivery pumps, or any of the relative positions of the components of the present invention, the terms "axial" or "axially" refer generally to a longitudinal axis "A" around which the mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the drug pumps. According to various aspects and embodiments described herein, reference is made to a "biasing member", such as in the context of one or more biasing members for asserting force on a plunger seal. It will be appreciated that the biasing member may be any member that is capable of storing and releasing energy. Non-limiting examples include a spring, such as for example a coiled spring, a compression or extension spring, a torsional spring, or a leaf spring, a resiliently compressible or elastic band, or any other member with similar functions. In at least one embodiment of the present invention, the biasing member is a spring, preferably a compression spring.

The novel devices of the present invention provide fluid restriction mechanisms to control (by restriction) the rate of drug delivery and drug delivery pumps which incorporate such fluid restriction mechanisms. Such drug delivery devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pumps, fluid control mechanisms, and their respective components are described further herein with reference to the accompanying figures.

Figure 1B:
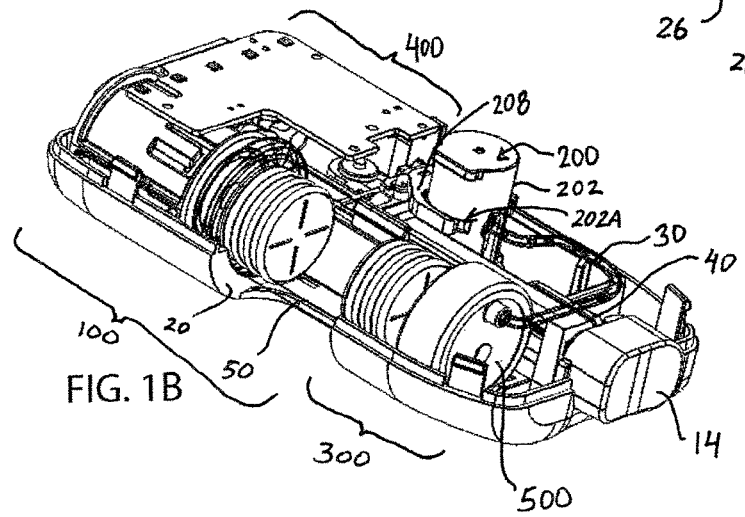
FIG. 1B shows an isometric view of the interior components of the drug delivery pump shown in FIG. 1A (shown without the adhesive patch)
Figure 1C:
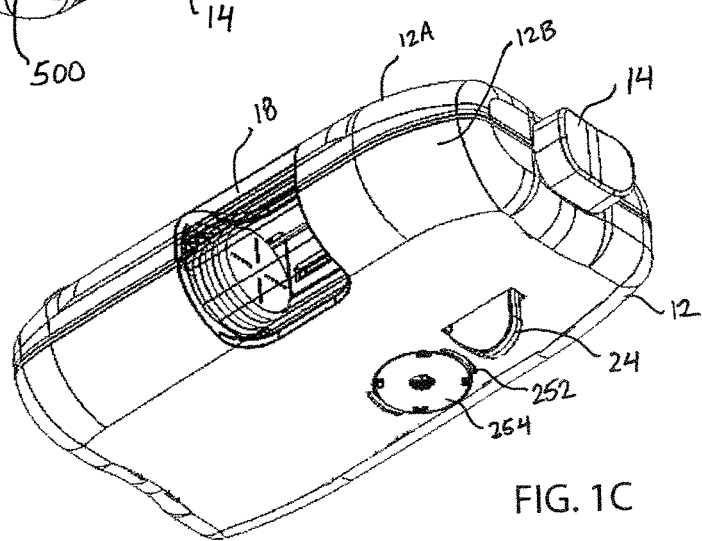
FIG. 1C shows an isometric view of the bottom of the drug delivery pump shown in FIG. 1A (shown without the adhesive patch)

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device according to at least one embodiment of the present invention. The drug delivery device may be utilized to administer delivery of a drug treatment into a body of a user. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump further includes assembly platform 20, sterile fluid conduit 30, drive mechanism 100 having drug container 50, insertion mechanism 200, fluid pathway connection 300, and power and control system 400. The fluid restriction mechanism 500 may be connected to the sterile fluid conduit 30, preferably, between the fluid pathway connection 300 and the insertion mechanism 200. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the skin of the user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as status indicator 16 and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12, such as through an aperture between upper housing 12A and lower housing 12B, and which contacts a control arm 40 of the power and control system 400. In at least one embodiment, the start button 14 may be a push button, and in other embodiments, may be an on/off switch, a toggle, or any similar activation feature known in the art. The pump housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug pump 10 is placed on the body of the user. Housing 12 is described in further detail hereinafter with reference to other components and embodiments of the present invention.

The drug pump is configured such that, upon activation by a user by depression of the activation mechanism, the drug pump is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug pump. For example, an optional on-body sensor 24 (shown in FIG. 1C) may be provided in one embodiment as a safety feature to ensure that the power and control system 400, or the activation mechanism, cannot be engaged unless the drug pump 10 is in contact with the body of the user. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Power and Control System:

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm 40 to identify when the on-body sensor 24 and/or the activation mechanism 14 have been activated. The power and control system 400 may also interface with the status indicator 16 of the pump housing 12, which may be a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the user, the power and control system 400 will power the drive mechanism 100 to begin delivery of the drug treatment through the fluid pathway connection 300 and sterile fluid conduit 30. In a preferred embodiment of the present invention, the insertion mechanism 200 and the fluid pathway connection 300 may be caused to activate directly by user operation of the activation mechanism 14. During the drug delivery process, the power and control system 400 is configured to provide a dispensing status signal via the status indicator 16. After the drug has been administered into the body of the user and after the end of any additional dwell time, to ensure that substantially the entire dose has been delivered to the user, the power and control system 400 may provide an okay-to-remove status signal via the status indicator 16. This may be independently verified by the user by viewing the drive mechanism and drug dose delivery through the window 18 of the pump housing 12. Additionally, the power and control system 400 may be configured to provide one or more alert signals via the status indicator 16, such as for example alerts indicative of fault or operation failure situations.

The power and control system 400 may additionally be configured to accept various inputs from the user to dynamically control the drive mechanisms 100 to meet a desired drug delivery rate or profile. For example, the power and control system 400 may receive inputs, such as from partial or full activation, depression, and/or release of the activation mechanism 14, to set, initiate, stop, or otherwise adjust the control of the drive mechanism 100 via the power and control system 400 to meet the desired drug delivery rate or profile. Similarly, the power and control system 400 may be configured to receive such inputs to adjust the drug dose volume; to prime the drive mechanism, fluid pathway connection, and fluid conduit; and/or to start, stop, or pause operation of the drive mechanism 100. Such inputs may be received by the user directly acting on the drug pump 10, such as by use of the activation mechanism 14 or a different control interface, or the system 400 may be configured to receive such inputs from a remote control device. Additionally or alternatively, such inputs may be pre-programmed.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Insertion Mechanism:

A number of insertion mechanisms may be utilized within the drug pumps of the present invention. The pump-type delivery devices of the present invention may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present invention.

In at least one embodiment, the insertion mechanism 200 includes an insertion mechanism housing having one or more lockout windows, and a base for connection to the assembly platform and/or pump housing (as shown in FIG. 1B and FIG. 1C). The connection of the base to the assembly platform 20 may be, for example, such that the bottom of the base is permitted to pass-through a hole in the assembly platform to permit direct contact of the base to the body of the user. In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to sterile fluid conduit 30 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 254 (shown in FIG. 1C).

According to at least one embodiment of the present invention, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. As shown in FIG. 1B, the lockout pin(s) 208 may be directly displaced by user depression of the activation mechanism 14. As the user disengages any safety mechanisms, such as an optional on-body sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 208 from their initial position within locking windows 202A of insertion mechanism housing 202. Displacement of the lockout pin(s) 208 permits insertion biasing member to decompress from its initial compressed, energized state. This decompression of the insertion biasing member drives the needle and the cannula into the body of the user. At the end of the insertion stage, the retraction biasing member is permitted to expand in the proximal direction from its initial energized state. This axial expansion in the proximal direction of the retraction biasing member retracts the needle, while maintaining the cannula in fluid communication with the body of the user. Accordingly, the insertion mechanism may be used to insert a needle and cannula into the user and, subsequently, retract the needle while retaining the cannula in position for drug delivery to the body of the user.

Drive Mechanism:

A number of drive mechanisms may be utilized to force fluid from a drug container for delivery into the body of a user. In one such embodiment, the drive mechanism 100 may be substantially similar to that described in International Patent Application No. PCT/US2012/053241, which is included by reference herein in its entirety for all purposes. As shown in FIG. 2A, a drug container may have a drug chamber 21 within the barrel 58 between a sliding pierceable seal 56 and a plunger seal 60. The drug chamber 21 may contain a drug fluid for delivery through integrated sterile fluid pathway connection, the fluid restriction mechanism, the insertion mechanism, and drug pump into the body of the user. The seals described herein may be comprised of a number of materials but are, in a preferred embodiment, comprised of one or more elastomers or rubbers. The drive mechanism 100 may contain one or more drive biasing members to drive the plunger seal 60. The components of the drive mechanism function to force a fluid from the drug chamber 21 out through fluid pathway connection 300, through the fluid restriction mechanism 500 where it may be controlled by restriction or by increased fluid travel time through the fluid pathway, to the sterile fluid conduit 30, and insertion mechanism 200 into the body of the user. For clarity, the fluid restriction mechanism 500 may be an aspect or component of the sterile fluid pathway connection 300 or be a separate component, as detailed further herein. The fluid restriction mechanism 500 may be connected at the beginning of the fluid conduit 30, between the sterile fluid pathway connection 300 and the fluid conduit 30, at the end of the fluid conduit 30, between the fluid conduit 30 and the insertion mechanism 200, or anywhere in between along the fluid conduit 30.

In one particular embodiment, the drive mechanism 100 employs one or more compression springs as the biasing member(s). Upon activation of the drug pump by the user, the power and control system 400 may be actuated to directly or indirectly release the compression spring(s) from an energized state. Upon release, the compression spring(s) may bear against and act upon the plunger seal 60 to force the fluid drug out of the drug chamber 21 of the drug container. Once the sterile fluid pathway connection 300 is connected or opened, drug fluid is permitted to flow from the drug container, through the sterile fluid pathway connection, fluid restriction mechanism, sterile fluid conduit, and insertion mechanism, and into the body of the user for drug delivery.

Fluid Pathway Connection:

A number of fluid pathway connections may be utilized within the embodiments of the present invention. Generally, a suitable fluid pathway connection includes a sterile fluid conduit, a piercing member, and a sterile sleeve attached to a drug container or a sliding pierceable seal integrated within a drug container. The fluid pathway connection may further include one or more flow restrictors. Upon proper activation of the device 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present invention, the piercing member of the fluid pathway connection is caused to penetrate the pierceable seal of the drug container of the drive mechanism by direct action of the user, such as by depression of the activation mechanism by the user. For example, the activation mechanism itself may bear on the fluid pathway connection such that displacement of the activation mechanism from its original position also causes displacement of the fluid pathway connection. In one such embodiment, the fluid pathway connection may be substantially similar to that described in International Patent Application No. PCT/US2012/054861, which is included by reference herein in its entirety for all purposes. According to such an embodiment, the connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connection may be integrated into a drug container as described in International Patent Application No. PCT/US2013/030478, for example, which is included by reference herein in its entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The sliding pierceable seal is caused to slide towards the cap, causing it to be pierced by the piercing member retained within the integrated sterile fluid pathway connection. Accordingly, the integrated sterile fluid pathway connection is connected (i.e., the fluid pathway is opened) by the combination pneumatic/hydraulic force of the air/gas and drug fluid within the drug chamber created by activation of a drive mechanism. Once the integrated sterile fluid pathway connection is connected or opened, drug fluid is permitted to flow from the drug container, through the integrated sterile fluid pathway connection, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

Regardless of the fluid pathway connection utilized by the drug pump, the drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connection 300 and the sterile fluid conduit 30 are provided hereinafter in later sections in reference to other embodiments.

Fluid Restriction Mechanism:

The fluid restriction mechanisms of the present invention may take a number of configurations while remaining within the scope of the presently claimed embodiments. The fluid restriction mechanisms provide a means for fluid delivery control, by restricting the flow of fluid travel and/or by increasing the length of the fluid pathway that the fluid must travel through between the drug container and the insertion mechanism before delivery into the patient. The fluid restriction mechanisms of the present invention are readily replaceable, configurable, and/or stackable to enable the drug delivery device to meet the desired drug delivery profile (e.g., delivery duration). The fluid restriction mechanism 500 may be connected to the sterile fluid conduit 30, preferably, between the fluid pathway connection 300 and the insertion mechanism 200. For example, the fluid restriction mechanism 500 may be connected at the beginning of the fluid conduit 30 (between the sterile fluid pathway connection 300 and the fluid conduit 30), at the end of the fluid conduit 30 (between the fluid conduit 30 and the insertion mechanism 200), or anywhere in between along the fluid conduit 30.

The fluid restriction mechanism 500 resides within the housing of the drug pump, as shown in FIG. 1B. FIG. 2A shows an isometric view of a fluid restriction mechanism, according to at least one embodiment of the present invention, attached to an integrated sterile fluid pathway connection and drug container. In such an embodiment, the fluid restriction mechanism may be a component of the integrated sterile fluid pathway connection and drug container. As shown in FIG. 2B, the fluid restriction mechanism may be attached to the sterile fluid pathway connection and drug container, such as by retention by cap 52 which may be a cap that is crimped to the barrel 58. In this configuration, the fluid restriction mechanism may include a piercing member 510, such as a needle, that is capable of piercing a seal 56 of the sterile fluid pathway connection 300 to permit fluid flow from the drug chamber 21 of barrel 58 of the drug container 50. In this configuration, the seal 56 is caused to slide upon, and be pierced by the piercing member 510 upon hydraulic and/or pneumatic pressure of the fluid within the drug chamber 21 that is caused by a drive mechanism 100 (shown in FIG. 1C) acting upon plunger seal 60. Once the sterile fluid pathway connection 300 is opened, drug fluid may travel through piercing member 510, through the fluid channel(s) of the fluid restriction mechanism 500, out through port 512 through the fluid conduit 30 to the insertion mechanism 200 for drug delivery to the patient. FIG. 2C shows a side view of the fluid restriction mechanism shown in FIG. 2A. As will be detailed further herein, the fluid restriction mechanism 500 may also include a membrane 309, such as a partially permeable membrane, that is capable of venting air or other gas from the sterile cavity between the fluid restriction mechanism 500 and the seal 56. In such a configuration, the fluid restriction mechanism 500 does not need to move or translate once assembled to barrel 58 of the drug container 50 as the sterile fluid pathway connection 300 occurs integrated within the drug container 50. This configuration of the fluid restriction mechanism may be preferred for use with the integrated fluid pathway connection and drug container described in International Patent Application No. PCT/US2013/030478.

FIG. 3A shows an isometric view of a fluid restriction mechanism, according to another embodiment of the present invention. In this configuration, the fluid restriction mechanism 1500 is attached to a sterile fluid pathway connection which may or may not be integrated within the drug container. In this configuration, the seal 56 may be retained in position at the distal end of the barrel 58 by cap 52, and the sterile fluid pathway connection 300 may be external (i.e., not integrated) to the barrel 58 of the drug container 50. This configuration of the fluid restriction mechanism may be preferred for use with the fluid pathway connection and drug container described in International Patent Application No. PCT/US2012/054861. The fluid restriction mechanism 1500 of this embodiment may be attached to the distal end of the sterile fluid pathway connection 300 which is capable of acting upon and piercing the seal 56 retained within barrel 58 of the drug container 50. In that embodiment, the piercing member 1510 would instead be a conduit or port connected to the distal surface of the fluid pathway connection. Alternatively, a piercing member 1510 may be utilized in this embodiment to function as part of the integrated fluid pathway connection and drug container, and to pierce the seal 56 to permit drug flow from the drug container 50. FIG. 3B shows an exploded isometric view of the fluid restriction mechanism, and sterile fluid pathway connection and drug container, shown in FIG. 3A. FIG. 3C shows a side view of the fluid restriction mechanism shown in FIG. 3A.

FIG. 4A shows an exploded isometric view of the fluid restriction mechanism shown in FIGS. 2A-2C. Though the description below provides details with reference to the embodiments shown in FIGS. 2A-2C, the description with reference to the function of the fluid restriction mechanism may also provide detail to the embodiments shown in FIGS. 3A-3C. FIG. 4A shows the fluid restriction mechanism 500 as two separate components. FIG. 4B shows another angle of the exploded isometric view of the fluid restriction mechanism shown in FIG. 4A. As would be understood by one having ordinary skill in the relevant art, this is primarily for ease of manufacture and the mechanism 500 may be a single unified component if manufactured, for example, by injection molding or other suitable means. In this two-part assembly the fluid channel(s) may be imparted, such as by carving or other suitable means of manufacture, onto a first component 500B of the fluid restriction mechanism and then closed by attachment of a second component 500A. The two components may be affixed and held together by snap arms, adhesives, etc., or other mechanisms which are readily known in the industry to provide a tight seal to the fluid channel(s) of the fluid restriction mechanism. The second component (e.g., cover plate) 500A may be fused, molded, or otherwise connected to the first component (e.g., restriction plate) 500B. The fluid pathway of each of the fluid channels may be adjusted for pathway thickness, length, curvature, and any number of tortuous path parameters, for example, to produce a fluid restriction of any desired range. The pathway that a drug fluid may travel through the fluid restriction mechanism 500 is shown with reference to FIG. 4C, which provides a cross-sectional view of the fluid restriction mechanism shown in FIGS. 4A-4B. Drug fluid may enter the fluid restriction mechanism 500 through aperture 520A of a piercing member 510. The drug fluid then enters the fluid channel(s) at entry point 520B. The drug fluid is retained in the fluid channel(s) 520C because of the tight seal provided by the mating of the second component 500A to the first component 500B.

In the embodiment shown, the fluid channel(s) are in a spiral shape to elongate the length of travel that the fluid must pass (i.e., extending the time or duration of drug delivery). The width of the channel(s) may also be modified and utilized to control the flow parameters through the fluid restriction mechanism. The drug fluid then travels through the fluid channel(s) 520C to exit point 520D, at which point the drug fluid is caused to travel through outlet aperture 514 of port 512 to the fluid conduit 30 (visible in FIGS. 2A-2C). The fluid channel(s) may be shortened or lengthened to provide the desired duration of fluid delivery time (i.e., the drug fluid may be caused to travel a longer path or a shorter path through the fluid restriction mechanism). Additionally or alternatively, the fluid channel(s) may restrict the flow of drug fluid by functioning as an orifice. As would be readily understood by an ordinarily skilled artisan in the relevant arts, fluid flow in a pipe or conduit is always accompanied by friction of fluid particles rubbing against one another, and consequently, by loss of energy available for work. In other words, there must be a pressure drop in the direction of flow. Accordingly, the fluid channel(s) of the fluid restriction mechanism may function as an orifice to meter rate of flow, by restricting flow and/or to reduce pressure. For liquid flow, several orifices are sometimes used to reduce pressure in steps so as to avoid cavitation. Concurrently, a vent aperture 530A, 530B may be utilized to vent the air or gas from the proximal side of the fluid restriction mechanism 500 to the distal side of the fluid restriction mechanism 500. A membrane 309, such as a partially permeable membrane, may be utilized for example to facilitate the passage of gas (e.g., air) in one direction while preventing fluid passage therethrough.

Figure 5A:
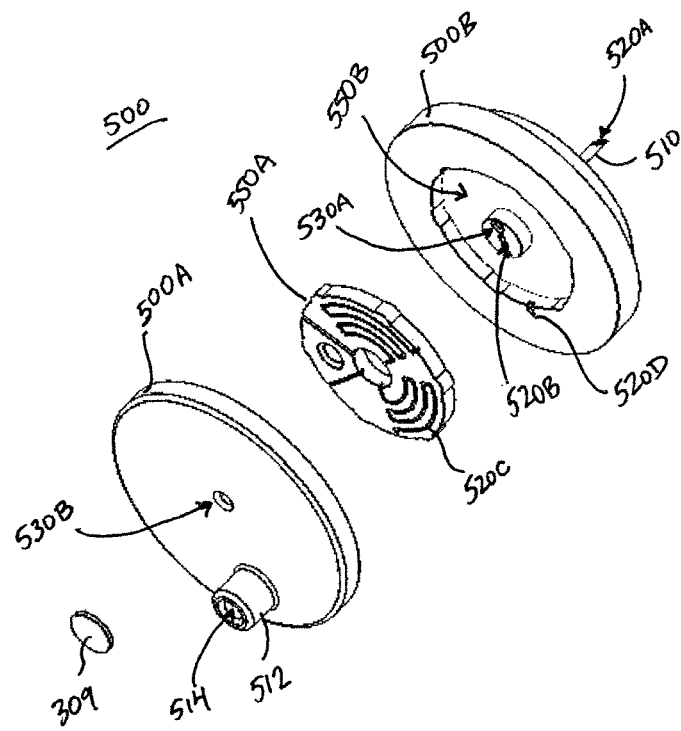
FIG. 5A shows an exploded isometric view of a configurable fluid restriction mechanism, according to another embodiment of the present invention.
Figure 5B:
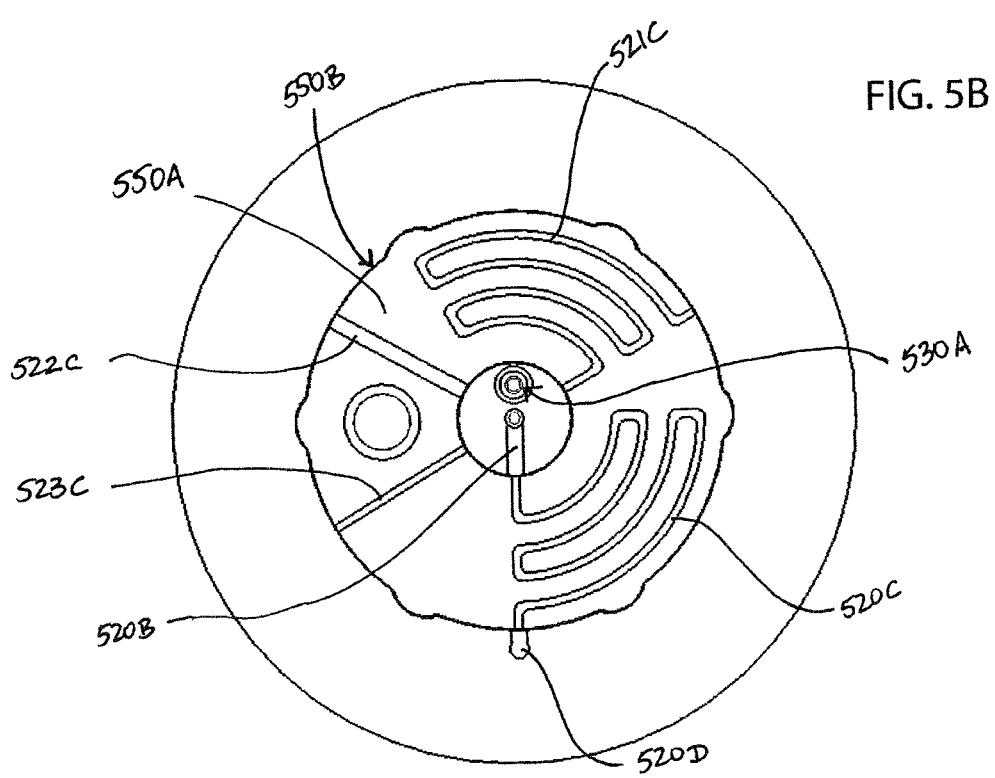
FIG. 5B shows a front view of the configurable fluid restriction mechanism shown in FIG. 5A.

FIGS. 5A-5B show a configurable fluid restriction mechanism, according to another embodiment of the present invention, in the exploded and front views respectively. In this embodiment, the fluid restriction mechanism 500 contains more than one fluid channel 520C, 521C, 522C, and 523C. Accordingly, the same fluid restriction mechanism 500 may be utilized in a number of configurations to provide the desired fluid flow parameters. If shorter drug delivery duration is desired, channel 522C may be selected and aligned with entry point 520B and exit point 520D. If more restrictive fluid flow is desired, channel 523C may be selected and aligned with entry point 520B and exit point 520D. Alternatively, channels 521C or 520C may be selected and aligned with entry point 520B and exit point 520D to reach the desired drug delivery parameters. This is facilitated, for example during assembly of the device, by identifying the desired drug delivery parameters and the appropriate fluid channel, and rotating and mounting the fluid chip 550A into the corresponding recess 550B such that the selected fluid channel aligns with entry point 520B and exit point 520D. This is shown in FIG. 5B.

Any number of distinct channels may be provided and utilized in this embodiment of a configurable fluid restriction mechanism. Additionally, the desired channels may be opened or closed by removing or adding, respectively, barriers between the channels. For example, if an even longer fluid channel is desired, the barriers between channels 521C and 520C may be modified such that the fluid flows initially into channel 520C through entry point 520B, then through channel 521C, then back through the remainder of channel 520C to exit point 520D. In a further embodiment, the fluid restriction plate may have a number of sequential or parallel pathways which are configurable to deliver the desired fluid restriction parameters. For example, the fluid restriction plate may have a number of different pathways of different lengths and constraints, and the specifically desired fluid pathway may be selected during assembly to produce the desired fluid restriction for the drug pump system. One or more of these pathways may be "opened" or "closed" prior to assembly to enable a range of configurable fluid pathways. While plates are discussed and shown herein, the fluid restrictors may take on a number of different shapes and configurations including, but not limited to, spheres, discs, pucks, semicircles, rectangles, cubes, pyramids, and the like. This configurability provides even more variation to the number of channels or fluid path configurations capable of being employed by the present invention. More complex shapes may be utilized which include different fluid pathway channels, and these are only restricted by economically-feasible and known manufacturing methods. For example, more complex shapes and fluid channel configurations may be possible via 3D-printing, or other complex manufacturing methods. Concurrently, a vent aperture 530A, 530B may be utilized to vent the air or gas from the proximal side of the fluid restriction mechanism 500 to the distal side of the fluid restriction mechanism 500. A membrane 309, such as a partially permeable membrane, may be utilized for example to facilitate the passage of gas (e.g., air) in one direction while preventing fluid passage therethrough.

FIG. 6A shows an isometric view of a stackable fluid restriction mechanism, according to another embodiment of the present invention. FIG. 6B shows an exploded isometric view of the stackable fluid restriction mechanism. The stackable fluid restriction mechanism may utilize any of the fluid restriction arrangement described above with reference to FIG. 4A and FIG. 5A, in the configurations shown in FIGS. 2A-2C, FIGS. 3A-3C, or the other configurations described herein. Accordingly, one or more fluid restriction mechanisms may be utilized in a stacked configuration to provide an additional distance that the drug fluid must travel to prolong the duration of drug delivery. In such a stacked configuration, a spacer plate 503B may be utilized between two restriction plates 503A and 500B, in order to align the fluid entry points and exit points with the corresponding or abutting plates. Any number of these plates may be utilized to reach the desired drug delivery parameters.

Figure 7A:
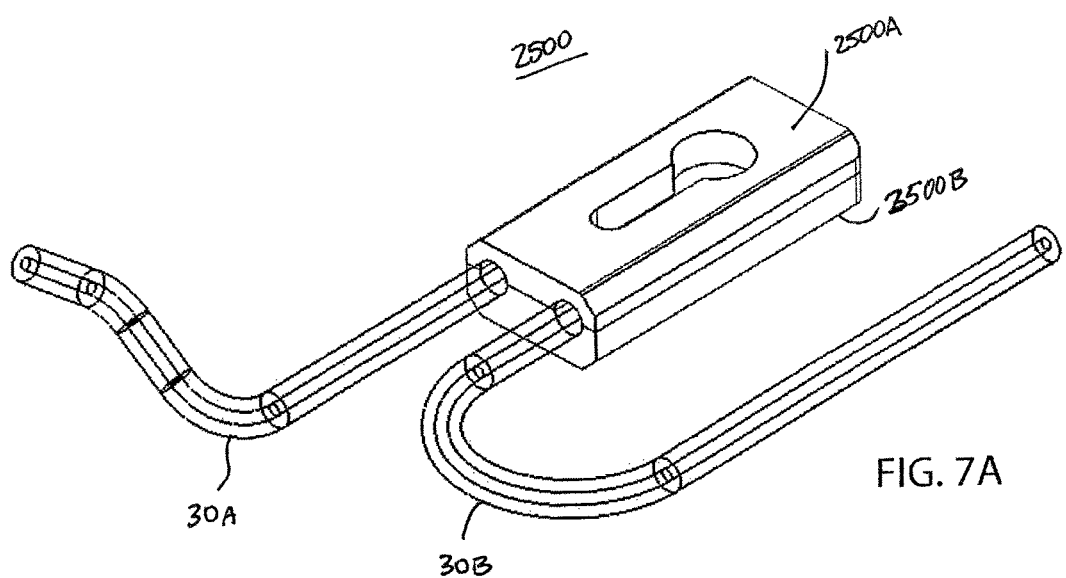
FIG. 7A shows an isometric view of a fluid restriction mechanism, according to a further embodiment of the present invention.
Figure 7B:
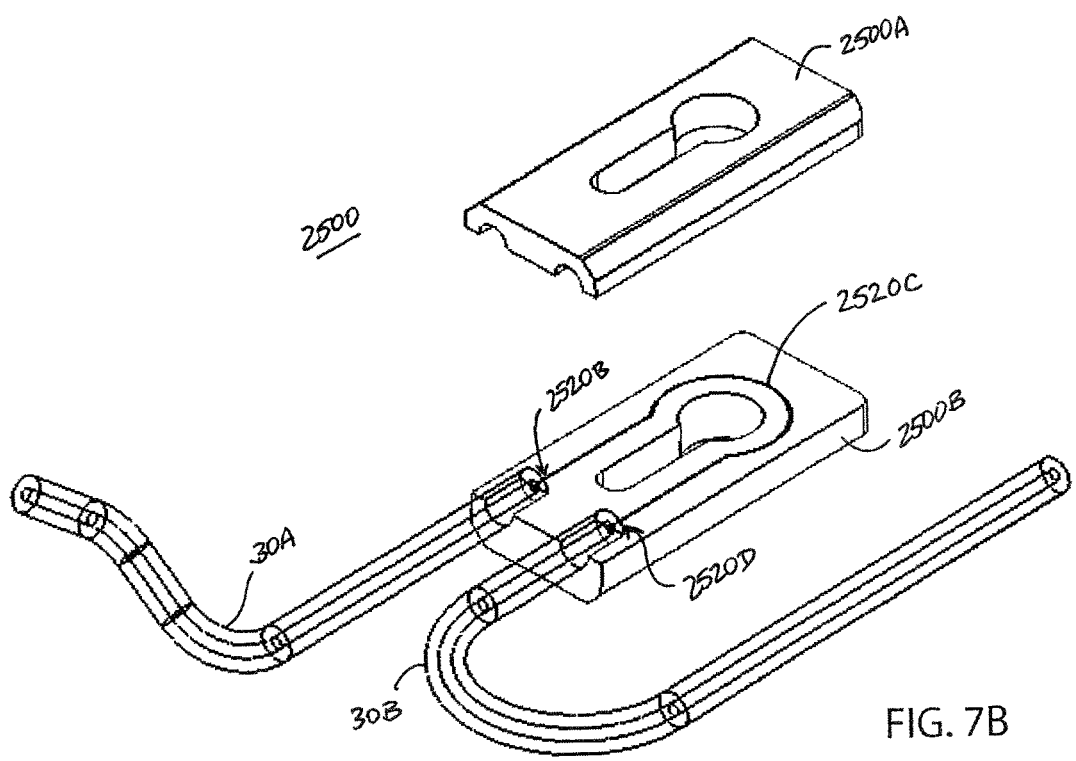
FIG. 7B shows the isometric view of the fluid restriction mechanism shown in FIG. 7A, with the top component of the fluid restriction mechanism removed.

The fluid restriction mechanisms of the present invention are shown primarily in a disc-shaped configuration, though the shape is not a necessary limitation on the present invention and any number of known shapes may be utilized. For example, FIG. 7A shows an isometric view of a rectangular fluid restriction mechanism, according to a further embodiment of the present invention. FIG. 7B shows the isometric view of the fluid restriction mechanism shown in FIG. 7A, with the top component of the fluid restriction mechanism removed. As shown, the fluid restriction mechanism may take any number of shapes or dimensions, provided that there is at least one fluid channel therein having at least one entry point and at least one exit point through which the drug fluid may travel. Additionally, the fluid restriction mechanism 500 may be connected to the sterile fluid conduit 30, preferably, between the fluid pathway connection 300 and the insertion mechanism 200. For example, the fluid restriction mechanism 500 may be connected at the beginning of the fluid conduit 30 (between the sterile fluid pathway connection 300 and the fluid conduit 30), at the end of the fluid conduit 30 (between the fluid conduit 30 and the insertion mechanism 200), or anywhere in between along the fluid conduit 30 (as shown in FIG. 7A-7B).

Assembly and/or manufacturing of fluid restriction mechanism 500, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

A fluid pathway connection, and specifically a sterile sleeve of the fluid pathway connection, may be connected to the cap and/or pierceable seal of the drug container. The fluid restriction mechanism may be connected to the other end of the fluid pathway connection. A fluid conduit may be connected to the fluid restriction mechanism at one end and the insertion mechanism at the other end, such that the fluid pathway, when opened, connected, or otherwise enabled travels directly from the drug container, fluid pathway connection, fluid restriction mechanism, fluid conduit, insertion mechanism, and through the cannula for drug delivery into the body of a user. As described above, the fluid restriction mechanism may alternatively be located between the sterile pathway connection and the insertion mechanism such that a first fluid conduit is connected directly to the sterile pathway connection and to the fluid restriction mechanism, and then a second fluid conduit is connected to the fluid restriction mechanism and to the insertion mechanism. Regardless of the configuration, or order of components, the fluid pathway, when opened, connected, or otherwise enabled travels directly from the drug container, fluid pathway connection, fluid restriction mechanism, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug pump, as shown in FIG. 1B.

Certain optional standard components or variations of fluid restriction mechanism 500 or drug pump 10 are contemplated while remaining within the breadth and scope of the present invention. For example, the drug pump 10 may contain an adhesive patch 26 and a patch liner 28 on the bottom surface of the housing 12. The adhesive patch 26 may be utilized to adhere the drug pump 10 to the body of the user for delivery of the drug dose. As would be readily understood by one having ordinary skill in the art, the adhesive patch 26 may have an adhesive surface for adhesion of the drug pump to the body of the user. The adhesive surface of the adhesive patch 26 may initially be covered by a non-adhesive patch liner 28, which is removed from the adhesive patch 26 prior to placement of the drug pump 10 in contact with the body of the user. Removal of the patch liner 28 may further remove the sealing membrane 254 of the insertion mechanism 200, opening the insertion mechanism to the body of the user for drug delivery (as shown in FIG. 1C).

Similarly, one or more of the components of fluid restriction mechanism 500 and drug pump 10 may be modified while remaining functionally within the breadth and scope of the present invention. For example, as described above, while the housing of drug pump 10 is shown as two separate components upper housing 12A and lower housing 12B, these components may be a single unified component. As discussed above, a glue, adhesive, or other known materials or methods may be utilized to affix one or more components of the fluid restriction mechanism and/or drug pump to each other. Alternatively, one or more components of the fluid restriction mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. A drug delivery pump with fluid delivery control comprising:
    a housing, within which are mounted:
        an activation mechanism,
        an insertion mechanism configured to introduce a needle or cannula to a target,
        a drug container having a plunger seal and a pierceable seal,
        a drive mechanism,
        a fluid pathway connection having a piercing member configured to penetrate the pierceable seal to permit fluid flow, and
        a fluid restriction mechanism;
        the drug container being connected at one end to a drive mechanism and at another end to a fluid pathway connection,
        the fluid restriction mechanism being connected at one end to the fluid pathway connection and at the other end to a fluid conduit,
        the fluid conduit being connected at another end to the insertion mechanism such that the fluid restriction mechanism is positioned to restrict or control a flow of a drug fluid from the drug container to the insertion mechanism, and
    the fluid restriction mechanism comprising:
        an aperture residing adjacent to the fluid pathway connection and configured to permit flow of a drug fluid through the aperture when the fluid pathway connection is open,
        an entry point,
        an exit point,
        a fluid channel configured to permit flow of the drug fluid through the aperture to the entry point and through the fluid channel to the exit point,
        an outlet aperture through which the flow of drug fluid can travel after exiting the exit point,
        a vent aperture; and
        a membrane at the vent aperture configured to permit air or gas to exit the fluid restriction mechanism while preventing fluid passage therethrough.

2. The drug delivery pump of claim 1, wherein the membrane is a permeable membrane.

3. The drug delivery pump of claim 1, wherein more than one fluid restriction mechanism is connected in series in a stacked configuration, the aperture of a first fluid restriction mechanism residing adjacent to the fluid pathway connection and configured to permit flow of the drug fluid through the aperture when the fluid pathway connection is open, the fluid conduit connected to the outlet aperture of a last fluid restriction mechanism in the stacked configuration.

4. The drug delivery pump of claim 1, wherein the fluid restriction mechanism further comprises:
    a plurality of fluid channels selectably alignable with the entry point and the exit point of the fluid restriction mechanism.

5. The drug delivery pump of claim 4, wherein the plurality of fluid channels vary in length to provide different durations of travel for the flow of drug fluid.

6. The drug delivery pump of claim 4, wherein the plurality of fluid channels vary in diameter to provide different fluid restrictions to the flow of drug fluid.

7. The drug delivery pump of claim 4, wherein one or more fluid channels may be selectively opened to permit the flow of drug fluid.

8. The drug delivery pump of claim 4, wherein one or more fluid channels may be selectively closed to prevent the flow of drug fluid.

9. The drug delivery pump of claim 4, wherein one or more fluid channels may be connected to each other to increase the duration of travel that the drug fluid must flow through.

10. The drug delivery pump of claim 4, wherein the fluid restriction mechanism is in the shape of a disc, a spheroid, a square, a sphere, a cube, a rectangle, or a pyramid.

11. The drug delivery pump of claim 1, wherein the fluid restriction mechanism is a component of the fluid pathway connection mounted to and integrated within the barrel of the drug container.

12. The drug delivery pump of claim 1, wherein the fluid restriction mechanism is a component adjacent to the fluid pathway connection and configured to restrict flow of the drug fluid from a barrel of the drug container through the drug pump once the fluid pathway connection is opened.

13. The drug delivery pump of claim 1, wherein the fluid restriction mechanism is connected to the fluid pathway connection by a first fluid conduit, and the fluid restriction mechanism is connected to the insertion mechanism by a second fluid conduit, such that the flow of drug fluid is restricted between the drug container and the insertion mechanism by the fluid restriction mechanism.

14. The drug delivery pump of claim 1, wherein the piercing member is configured to translate relative to the pierceable seal.

\* \* \* \* \*